United States Patent [19]

Halbritter

[11] 4,189,592

[45] Feb. 19, 1980

[54] PREPARATION OF 4-METHYL-5-[(2-AMINOETHYL)-THIOMETHYL]-IMIDAZOLE DIHYDROCHLORIDE

[75] Inventor: Klaus Halbritter, Mannheim, Fed. Rep. of Germany

[73] Assignee: BASF Aktiengesellschaft, Fed. Rep. of Germany

[21] Appl. No.: 7,005

[22] Filed: Jan. 26, 1979

[30] Foreign Application Priority Data

Apr. 3, 1978 [DE] Fed. Rep. of Germany ....... 2814355

[51] Int. Cl.$^2$ .......................................... C07D 233/64
[52] U.S. Cl. ................................ 548/342; 548/146
[58] Field of Search ........................................... 548/342

[56] References Cited

U.S. PATENT DOCUMENTS

| | | | |
|---|---|---|---|
| 3,950,333 | 4/1976 | Durant et al. | 548/342 |
| 4,053,473 | 10/1977 | Durant et al. | 548/342 |
| 4,063,023 | 12/1977 | Anderson et al. | 548/342 |
| 4,112,234 | 9/1978 | Crenshaw et al. | 548/342 |
| 4,122,277 | 10/1978 | Sawa et al. | 548/342 |

FOREIGN PATENT DOCUMENTS 2211454 10/1972 Fed. Rep. of Germany ............ 548/342

1338169 11/1973 United Kingdom ...................... 548/342

OTHER PUBLICATIONS

Durant et al., J. Med. Chem. 1976, vol. 19, pp. 923–928.
Godefroi et al., Recueil des travaux chimiques des pays/bas, 1972, vol. 91, pp. 1383–1392.
Grindley et al., J. Chem. Soc. (London) 1927, pp. 3128–3136.
Ewins, J. Chem. Soc. (London) 1911, vol. 99, pp. 2052–2059.
Hofmann, Imidazole and Its Derivatives, Part I, pp. 99–100, N.Y., Interscience, 1953.
Masui et al., Chem. Pharm. Bull., 1974, vol. 22, pp. 2359–2364.
Windaus, Berichte (Deutsche Chem. Gesellschaft) 1909, vol. 42, pp. 758–763.

*Primary Examiner*—Natalie Trousof
*Attorney, Agent, or Firm*—Keil & Witherspoon

[57] ABSTRACT

4-Methyl-5-[(2-aminoethyl)-thiomethyl]-imidazole dihydrochloride is prepared in a single-step process by thiomethylating 4-methylimidazole. The product is an intermediate for other imidazole derivatives, especially the drug cimetidine.

2 Claims, No Drawings

PREPARATION OF 4-METHYL-5-[(2-AMINOETHYL)-THIOMETHYL]-IMIDAZOLE DIHYDROCHLORIDE

The present invention relates to a single-step process for the preparation of 4-methyl-5-[(2-aminoethyl)-thiomethyl]-imidazole dihydrochloride by thiomethylating 4-methylimidazole.

It is known that 4-methyl-5-[(2-aminoethyl)-thiomethyl]-imidazole dihydrochloride can be prepared from 4-methyl-5-hydroxymethyl-imidazole hydrochloride by reaction with cysteamine hydrochloride in boiling acetic acid or boiling concentrated hydrochloric acid, as described, for example, in German Laid-Open Application DOS 2,211,454. It is a disadvantage of this process that the starting material is 4-methyl-5-hydroxymethyl-imidazole, since this compound can only be prepared by a relatively troublesome method involving reduction of 4-methylimidazole-5-carboxylic acid esters with lithium aluminum hydride (J.Med.Chem. 19 (1976), 923–928) or with alkali metals or calcium in liquid ammonia (German Laid-Open Application DOS 2,637,670). A two-stage process of preparation, in which 4-methyl-5-chloromethylimidazole hydrochloride is reacted with cysteamine hydrochloride, has also been proposed.

I have found that 4-methyl-5-[(2-aminoethyl)-thiomethyl]-imidazole dihydrochloride can be prepared by a single-stage process wherein 4-methylimidazole, in excess aqueous concentrated hydrochloric acid, is reacted with cysteamine and formaldehyde or formaldehyde oligomer, or with thiazolidone or bis-(N-thiazolidinyl)-methane, in a closed system, at from 110° to 170° C.

The process according to the invention can, for example, be represented by the following equation:

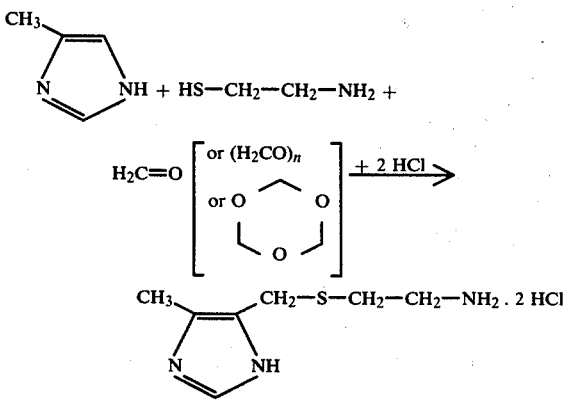

In the process according to the invention, it is advantageous to dissolve the 4-methylimidazole, cysteamine and formaldehyde or formaldehyde oligomer in aqueous concentrated hydrochloric acid; the solutions prepared as a rule contain from 20 to 40% by weight of the starting compounds. Advantageously, the starting compounds 4-methylimidazole, cysteamine and formaldehyde (considered as the monomer) are used in a molar ratio of 0.9–1.1:0.9–1.1:0.9–1.4. These molar ratios also apply when using thiazolidine or bis-(N-thiazolidinyl)-methane, which can be regarded as, respectively, 1:1 and 2:3 condensation products of cysteamine and formaldehyde.

The 4-methylimidazole may be used in the form of the pure substance or as a conventional technical-grade product of about 92–98% purity. The cysteamine is employed as the base or as the hydrochloride.

The formaldehyde can be employed as a gas or as a conventional aqueous solution containing from 30 to 40% by weight of formaldehyde, as paraformaldehyde or as s-trioxane.

In a particular embodiment of the process according to the invention, the condensation products of cysteamine and formaldehyde, i.e. thiazolidine or bis-(N-thiazolidinyl)-methane or their hydrochlorides, are reacted with 4-methylimidazole under the conditions according to the invention. In the case of the reaction of thiazolidine it can be advantageous to incorporate into the reaction mixture an additional amount of formaldehyde or formaldehyde oligomer, for example about 5 to 20, preferably about 10 mole %, based on the thiazolidine.

The hydrogen chloride is used in excess, advantageously in the form of aqueous concentrated hydrochloric acid containing from 30 to 40% by weight of hydrogen chloride. As a rule, the molar concentration of hydrogen chloride is from 3 to 8 times of the 4-methylimidazole. Where aqueous formaldehyde solution is used, HCl gas can, if desired, be additionally introduced into the reaction solution until the desired concentration is reached.

The thiomethylation reaction according to the invention is carried out in a closed system, for example in a glass-lined kettle or tantalum autoclave, at from 110° to 170° C., preferably from 115° to 145° C. The pressure generated in the closed system is the autogenous pressure for the particular temperature used, and is as a rule from about 0.5 to 12 bar and from 3.5 to 5.5 bar in the prefered temperature range.

The reaction is in general complete within from 5 to 30 hours. The course of the reaction can readily be followed spectroscopically, for example by analyzing samples by MNR spectroscopy after treatment with D$_2$O.

The reaction product is worked up by conventional methods, for example by distilling off the solvent and recrystallizing the residue, for example from a lower alcohol of 1 to 4 carbon atoms, eg. ethanol or n-propanol, or from a lower carboxylic acid, eg. acetic acid. The residue can also be digested with one of the above solvents. If desired, the free base can also readily be prepared by conventional methods.

The single-stage process according to the invention is surprisingly simple. It was not to be expected that the reaction would take place in the manner we have found. Alkylthiomethylation reactions with cysteamine as the thiol are not disclosed in the literature. In general, only a few examples of alkylthiomethylations are described in the literature, as may be seen, for example, by reference to J. Mathieu and J. Weill-Raynal in Formation of C—C Bonds, Vol. 1, Georg Thieme Verlag, Stuttgart 1973. These examples are restricted exclusively to reactive carbocyclic aromatic compounds. An alkylthiomethylation of heterocyclic compounds, for example imidazoles, has not previously been described. Hence, the thiomethylation of 4-methylimidazole by mercaptoethylamine (cysteamine) was not foreseeable by those skilled in the art. Instead, the well-known reaction of formaldehyde with cysteamine hydrochloride to give thiazolidine hydrochloride would have been expected to occur:

 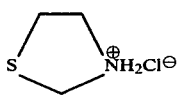

It is known that this thiazolidine formation reaction takes place under very mild conditions at room temperature, cf. S. Ratner and H. T. Clarke in J.Amer.Chem.Soc. 59 (1937), 200–206. The thiazolidine is even formed in high yield, as may be seen from Comparative Example 6, if cysteamine is reacted with paraformaldehyde in boiling aqueous concentrated hydrochloric acid in the presence of 4-methylimidazole.

As regards the 4-methylimidazole, a fact to be singled out particularly is that the thiomethylation takes place very selectively in the 5-position and not in the 2-position; furthermore, the conceivable aminomethylation side reactions are not observed.

A fact of particular practical importance is that the theoretically feasible formation of bis-chloromethyl ether is not observed in the process according to the invention.

By virtue of the invention, 4-methyl-5-[(2-aminoethyl)-thiomethyl]-imidazole dihydrochloride, an important intermediate for other imidazole derivatives, is now industrially more readily obtainable than hitherto.

4-Methyl-5-[(2-aminoethyl)-thiomethyl]-imidazole is an important intermediate, for example for the preparation of the drug cimetidine (N-cyano-N'-methyl-N''-[2-((4-methyl-5-imidazolyl)-methylmercapto)-ethyl]-guanidine), as described in German Laid-Open Applications DOS 2,344,779 and DOS 2,649,059.

The Examples which follow illustrate the process of the invention without implying any limitation.

EXAMPLE 1

42.0 Parts of 97.5% pure 4-methylimidazole, 56.8 parts of cysteamine hydrochloride and 18.0 parts of paraformaldehyde are dissolved in 207 parts of 37% strength aqueous hydrochloric acid, whilst cooling so that the temperature does not exceed 30° C. The mixture is heated in a closed glass-lined kettle for 5 hours at 110°–120° C. and for a further 10 hours at 120° C. The hydrochloric acid is then distilled off under reduced pressure from a water-pump, at not more than 80° C., until the residue has almost been reduced to dryness, after which the latter is dissolved in 237 parts of boiling ethanol. The solution is cooled to 20° C. and the precipitate which forms is filtered off and dried. 81.9 Parts (constituting the 1st fraction) of 4-methyl-5-[(2-aminoethyl)-thiomethyl]-imidazole dihydrochloride, of melting point 179°–180° C., are obtained.

The filtrate is evaporated to about half its volume and is cooled to 20° C., and the precipitate is filtered off. After drying, a further 12.7 parts (constituting the 2nd fraction) of melting point 149°–154° C. are obtained.

Fractions 1 and 2 are combined and recrystallized from 315 parts of glacial acetic acid. After drying at 10 mm Hg and 90° C., 82.4 parts (67.5%) of 4-methyl-5-[(2-aminoethyl)-thiomethyl]-imidazole dihydrochloride of melting point 190°–191° C. are obtained.

EXAMPLE 2

44.3 Parts of 92.5% pure 4-methylimidazole, 38.6 parts of cysteamine and 17.7 parts of paraformaldehyde are dissolved in 260 parts of 37% strength aqueous hydrochloric acid and the solution is heated for 20 hours at 140° C. in a closed glass-lined kettle. The hydrochloric acid is then distilled off under reduced pressure from a waterpump, at not more than 80° C., until the residue has almost been reduced to dryness, after which the latter is dissolved in 356 parts of boiling ethanol. The solution is cooled to 20° C. and the precipitate which forms is filtered off and dried. 74 Parts (61%) of product, of melting point 188°–190° C., are obtained.

The filtrate is concentrated to about half its volume and is cooled to 5° C. The precipitate is filtered off and dried, giving a further 12.3 parts (10%) of material, of melting point 181°–185° C.

Instead of crystallizing in two fractions, the reaction mixture, which has almost been reduced to dryness, can be digested for one hour while hot with 472 parts by volume of n-propanol (parts by volume relating to parts by weight as the liter to the kilogram), is filtered hot and the residue dried. 89.6 parts by weight (73.5% yield) of almost colorless crystals melting at 191.4°–193.6° C. are obtained.

EXAMPLE 3

27 Parts of 97% pure 4-methylimidazole, 37.5 parts of cysteamine hydrochloride and 10.8 parts of paraformaldehyde are dissolved in 124 parts of 37% strength aqueous hydrochloric acid and the mixture is heated for 10 hours at 150° C. in a closed tantalum autoclave. The hydrochloric acid is then distilled off under reduced pressure from a waterpump, at not more than 80° C., until the residue has almost been reduced to dryness, after which the latter is dissolved in 237 parts of boiling ethanol. After cooling to 20° C., the precipitate is filtered off, washed with 50 parts of ice-cold ethanol and dried. 53 parts (68%) of product, of melting point 186°–188° C., are obtained.

EXAMPLE 4

18.8 Parts by 93% pure 4-methylimidazole, 25.1 parts of thiazolidine hydrochloride and 0.9 part of paraformaldehyde in 95 parts of 37% strength hydrochloric acid are heated for 10 hours at 130° C. in a closed glass-lined kettle.

The hydrochloric acid is then distilled off, at not more than 80° C., until the residue has almost been reduced to dryness, after which the latter is dissolved in 237 parts of boiling ethanol. After cooling to 20° C., the precipitate is filtered off, washed with 40 parts of cold ethanol and dried. 26 parts (53%) of product, of melting point 188°–189° C., are obtained. On working up the mother liquor and then recrystallizing from glacial acetic acid, a further 8 parts (16%) of product, of melting point 188°–189° C., are obtained.

EXAMPLE 5

28.5 Parts of bis-(N-thiozolidinyl)-methane and 26.5 parts of 93% pure 4-methylimidazole are dissolved in 124 parts of 37% strength aqueous hydrochloric acid and the solution is heated for 10 hours at 130° C. in a closed glass-lined kettle. The hydrochloric acid is then distilled off at not more than 80° C., until the residue has almost been reduced to dryness, after which the latter is dissolved in 237 parts of boiling ethanol. After cooling to 20° C., the product is filtered off, washed with 40 parts of ethanol and dried. 41.2 Parts (56%) of product, of melting point 183°–185° C., are obtained.

On concentrating the filtrate to about 2/5 of its original volume, filtering off the precipitate and drying, a further 7 parts (10%) of product, of melting point 181°–184° C., are obtained.

Comparative Example under Atmospheric Pressure

A solution of 8.8 parts of 93% pure 4-methylimidazole, 7.7 parts of cysteamine and 3.0 parts of paraformaldehyde in 47.5 parts of 37% strength aqueous hydrochloric acid is boiled (at 106° C.) for 1 hour. It is then substantially concentrated under reduced pressure from a water-pump, 16 parts of ethanol are added and the mixture is heated to the boil. After it has cooled to 5° C., the crystals which have precipitated are filtered off, washed with 40 parts of cold ethanol and dried.

8.2 Parts (65%) of thiazolidine hydrochloride, of melting point 169°–171° C., are obtained. The analytically pure compound, when recrystallized from ethanol, melts at 180° C.

NMR-spectroscopic Examination shows that the crude product contains about 3% by weight of 4-methyl-5-[(2-aminoethyl)-thiomethyl]-imidazole dihydrochloride.

I claim:
1. A process for the preparation of 4-methyl-5-[(2-aminoethyl)-thiomethyl]-imidazole dihydrochloride, wherein 4-methylimidazole, in excess aqueous concentrated hydrochloric acid, is reacted with cysteamine and formaldehyde or a formaldehyde oligomer, or with thiazolidine or bis-(N-thiazolidinyl)-methane, in a closed system, at from 110° to 170° C.
2. A process as claimed in claim 1, wherein 4-methylimidazole, cysteamine and formaldehyde are reacted in the molar ratio of 0.9–1.1:0.9–1.1:0.9–1.4.

* * * * *